United States Patent
Wang (10) Patent No.: US 11,266,296 B2
(45) Date of Patent: Mar. 8, 2022

(54) LENSLESS ENDOSCOPE AND OTHER IMAGING DEVICES

(71) Applicant: C URCHIN TECHNOLOGIES LLC, Concord, MA (US)

(72) Inventor: Feiling Wang, Medford, MA (US)

(73) Assignee: C URCHIN TECHNOLOGIES LLC, Concord, MA (US)

( * ) Notice: Subject to any disclaimer, the term of this patent is extended or adjusted under 35 U.S.C. 154(b) by 0 days.

(21) Appl. No.: 15/519,829

(22) PCT Filed: Oct. 19, 2015

(86) PCT No.: PCT/US2015/056246
§ 371 (c)(1),
(2) Date: Apr. 17, 2017

(87) PCT Pub. No.: WO2016/061582
PCT Pub. Date: Apr. 21, 2016

(65) Prior Publication Data
US 2017/0245735 A1    Aug. 31, 2017

Related U.S. Application Data

(60) Provisional application No. 62/122,320, filed on Oct. 17, 2014.

(51) Int. Cl.
*A61B 1/07* (2006.01)
*G02B 23/24* (2006.01)
(Continued)

(52) U.S. Cl.
CPC ...... *A61B 1/00009* (2013.01); *A61B 1/00167* (2013.01); *A61B 1/07* (2013.01);
(Continued)

(58) Field of Classification Search
CPC ............ G02B 23/2453; G02B 23/26; G02B 23/2446; G02B 23/2469; G02B 26/06;
(Continued)

(56) References Cited

U.S. PATENT DOCUMENTS 3,556,085 A * 1/1971 Takahashi .......... A61B 1/00165
                                                                    600/129
5,751,340 A * 5/1998 Strobl ................ A61B 1/00165
                                                                    348/65

(Continued)

FOREIGN PATENT DOCUMENTS

CN       1681432 A      10/2005
JP       59-214818      5/1983
(Continued)

OTHER PUBLICATIONS

International Search Report and Written Opinion dated Feb. 3, 2016 for International Application No. PCT/US2015/056246, filed on Oct. 19, 2015 (10 pages).

(Continued)

*Primary Examiner* — John P Leubecker
(74) *Attorney, Agent, or Firm* — Perkins Coie LLP (57) ABSTRACT

Techniques, systems, and devices are disclosed for obtaining optical images of a targeted object or scene such as a person's organ or tissue based on a fiber bundle having imaging optical fibers and optical phase modulation for improved imaging quality without using an objective lens to receive light from a target. Among its applications is an endoscope that bears no lens at the distal end, which affords miniaturization and bendability, and that has adjustable focal distance.

49 Claims, 7 Drawing Sheets

(51) Int. Cl.
*G02B 23/26* (2006.01)
*G02B 26/06* (2006.01)
*A61B 1/00* (2006.01)
*A61B 5/00* (2006.01)
*A61B 5/20* (2006.01)

(52) U.S. Cl.
CPC ........ *A61B 5/0084* (2013.01); *G02B 23/2446* (2013.01); *G02B 23/2453* (2013.01); *G02B 23/2469* (2013.01); *G02B 23/26* (2013.01); *A61B 5/0086* (2013.01); *A61B 5/20* (2013.01); *A61B 5/42* (2013.01); *G02B 26/06* (2013.01)

(58) Field of Classification Search
CPC ...... G02B 26/08; G02B 21/0056; G02B 6/06; G02B 27/0068; A61B 1/00009; A61B 1/07; A61B 5/0084; A61B 1/00167; A61B 5/0086; A61B 5/42; A61B 5/20; A61B 1/00172; G01N 21/6456; G01N 21/4795; G02F 1/0115
See application file for complete search history.

(56) References Cited

U.S. PATENT DOCUMENTS

| | | | |
|---|---|---|---|
| 2003/0076571 A1* | 4/2003 | MacAulay | G02B 21/0028 359/237 |
| 2003/0156788 A1* | 8/2003 | Henning | A61B 5/0088 385/31 |
| 2005/0018185 A1 | 1/2005 | Genet et al. | |
| 2006/0215248 A1* | 9/2006 | Maram | G02B 27/46 359/239 |
| 2008/0007733 A1 | 1/2008 | Marks et al. | |
| 2008/0136742 A1 | 6/2008 | Tegreene et al. | |
| 2011/0137126 A1 | 6/2011 | French et al. | |
| 2011/0275899 A1 | 11/2011 | Tearney | |
| 2012/0201235 A1* | 8/2012 | Lim | A61B 1/00016 370/349 |
| 2012/0287400 A1 | 11/2012 | Utagawa | |
| 2013/0128346 A1 | 5/2013 | Sangu | |
| 2014/0064654 A1* | 3/2014 | Anand | G02B 21/0032 385/3 |
| 2014/0104618 A1 | 4/2014 | Potsaid et al. | |
| 2015/0015879 A1* | 1/2015 | Papadopoulos | G02B 23/26 356/301 |
| 2015/0112144 A1* | 4/2015 | Chen | A61B 1/00167 600/156 |

FOREIGN PATENT DOCUMENTS

| | | |
|---|---|---|
| JP | 2005024505 A | 1/2005 |
| JP | 2011507319 | 3/2011 |
| JP | 2011527218 | 10/2011 |
| WO | 2003065103 | 8/2003 |
| WO | 2015088102 A1 | 6/2015 |
| WO | 2015153982 A1 | 10/2015 |

OTHER PUBLICATIONS

Office Action for Japanese Patent Application No. 2017-539526, dated Dec. 12, 2017, 9 pages.
Office Action for Chinese Patent Application No. 201580069393.4, dated Aug. 28, 2018, 9 pages.
Supplementary European Search Report for European Patent No. EP 15 85 1190, dated Nov. 19, 2018, 11 pages.
Office Action for Japanese Patent Application No. 2017-539526, dated Jun. 20, 2018, 6 pages.
Liu, L., et al., "Adaptive phase-locked fiber array with wavefront phase tip-tilt compensation using piezoelectric fiber positioners," Proc. Of SPIE, US, SPIE, 2007, vol. 6708, 67080-1-K-12, 13 pages.

* cited by examiner

1. Optical fiber
2. Mode field

Fig. 3(b)

3. Pixel of wavefront modulator
4. Projected mode field

LENSLESS ENDOSCOPE AND OTHER IMAGING DEVICES

CROSS-REFERENCE TO RELATED APPLICATIONS

This patent document is a national phase application which claims the benefits and priority of International Patent Application No. PCT/US2015/056246, entitled "LENLESS ENDOSCOPE AND OTHER IMAGING DEVICES filed by Feiling Wang on Oct. 19, 2015, which claims the benefits and priority of U.S. Provisional Patent Application No. 62/122,320, entitled "LENSLESS ENDOSCOPE AND OTHER IMAGING DEVICES" filed by Feiling Wang on Oct. 17, 2014. The entire content of the aforementioned patent applications are incorporated by reference as part of the disclosure of this patent document.

TECHNICAL FIELD

This patent document relates to systems, devices, and processes that use light for imaging objects and medical applications.

BACKGROUND

Optical imaging techniques can be used in a wide range of applications to obtain images from a scene or object. In medical applications, optical imaging techniques can be used with reduced invasive effects or free of invasive effects. In various optical imaging systems, an objective lens is used between a targeted scene or object and the imaging module to collect light from the targeted scene or object to collect light from the targeted scene or object to be imaged.

SUMMARY

Techniques, systems, and devices are disclosed for obtaining optical images of a targeted object or scene such as a person's organ or tissue based on a fiber bundle having imaging optical fibers and optical phase modulation for improved imaging quality without using an objective lens to receive light from a target. The applications of the disclosed technology includes an endoscope that bears no lens at the distal end, which affords miniaturization and bendability, and that has adjustable focal distance.

In one aspect, an imaging device that uses light to image a scene is provided to include a plurality of optical fibers that directly collect light emanated by a scene and transport the collected light in segments in the optical fibers; a wavefront modulator located to receive collected light in segments from the optical fibers so that the collected light in segments in the optical fibers are incident on the wavefront modulator which adds or subtracts an optical phase to each individual collected light from each optical fiber to produce phase-modulated light segments, one segment per optical fiber; and an imaging array located to receive phase-modulated light segments from the wavefront modulator.

In another aspect, an endoscope that uses light to image a scene is provided to include one or more light sources to produce illumination light; a fiber bundle that includes a distal termination end and a proximal termination end, one or more illumination optical fibers that receives the illumination light from the one or more light sources at the proximal termination end to guide the illumination light to the distal termination end to illuminate a scene to be imaged, a plurality of imaging optical fibers that directly collect light from the scene at the distal termination end without using a lensing element to collect light from the scene into the distal termination end and guide the collected light to the proximal termination end; a wavefront modulator including a plurality of independently controllable phase modulation pixels to produce independently controllable phases, respectively, the wavefront modulator positioned relative to the proximal termination end of the fiber bundle to receive the collected light from the imaging optical fibers in such a way that the collected light exiting different imaging optical fibers is impinged upon different phase modulation pixels of the wavefront modulator, respectively, to produce phase-modulated light segments that corresponding to the imaging optical fibers, respectively; an optical sensor array of optical detectors located to receive the phase-modulated light segments from the wavefront modulator.

Such endoscope can be configured for different medical imaging applications, including, to name some examples, cardiology imaging to use the distal termination end to image an area of a person's heart, pulmonology imaging to use the distal termination end to image an area of a person's lung, gastroenterology imaging to use the distal termination end to image an area of a person's gastrointestinal tract, urology imaging to use the distal termination end to image an area of a person's urinary tract, endocrinology imaging to use the distal termination end to image an area of a person's endocrine gland, and ophthalmology imaging to use the distal termination end to image an interior area of a person's eye, such as the retina.

The above and other aspects and their implementations are described in greater detail in the drawings, the description and the claims.

DETAILED DESCRIPTION

Techniques, systems, and devices are described for implementing optical imaging in various applications including medical imaging devices and applications by using a fiber bundle having imaging optical fibers and by using optical phase modulation for improved imaging quality without using an objective lens to receive light from a target. The disclosed technology can be used in circumstances where it is desirable to form images without an objective lens. One example is endoscopy in which an objective lens at the distal end limits the miniaturization and the bendability of the instruments. It has been regarded, however, impractical to use a flexible optical fiber bundle to directly collect light from a scene because the optical fibers, due to their inhomogeneity, would randomize the wavefront that reaches the proximal end, as a consequence, images of the scene can no longer be formed.

Another significant limitation of the existing endoscopes is that the focal distance of these instruments is fixed. In other words, sharply focused images can only be obtained when the scene is located a fixed distance from the objective lens.

One implementation of the disclosed technology in this patent document is a method that allows images to be formed without the use of an objective lens. For example, an endoscope instrument can be constructed based on such a configuration without bearing an objective lens at its distal end and that has a variable focal distance. Such a "lensless" endoscope instrument can have useful medical endoscopy applications. For example, endoscope devices or systems can be configured based on the disclosed technology for different medical imaging applications, including, cardiology imaging to use the distal termination end to image an area of a person's heart, pulmonology imaging to use the distal termination end to image an area of a person's lung, gastroenterology imaging to use the distal termination end to image an area of a person's gastrointestinal tract, urology imaging to use the distal termination end to image an area of a person's urinary tract, endocrinology imaging to use the distal termination end to image an area of a person's endocrine gland, and ophthalmology imaging to use the distal termination end to image an interior area of a person's eye, such as the retina.

In the following the terms "optical waves" and "light" are used to represent electromagnetic waves of any wavelength including, nanometer waves, visible light waves, infrared waves, terahertz waves, micro waves, radio waves, as well as non-electromagnetic waves such as ultrasound waves.

Image formation, in various applications, can be treated as a diffraction process which some existing imaging systems require an optical wavefront be collected and transported as a whole and require such a whole optical wavefront to maintain its phase regularity. This can be difficult in practical applications and the degradation of the phase of the wavefront can reduce the image quality.

The technology disclosed herein can be used to allow the optical wavefronts emanated by a scene to be collected in segments and become incoherent in their relative phases before image formation. As illustrated in the examples below, the whole wavefront can be partitioned into segments by using a bundle of imaging optical fibers to separately collect a wavefront in segments and to separately control the optical phases of such segments to achieve a good image quality when such segments are converted into an image by a sensing array.

Figure 1:
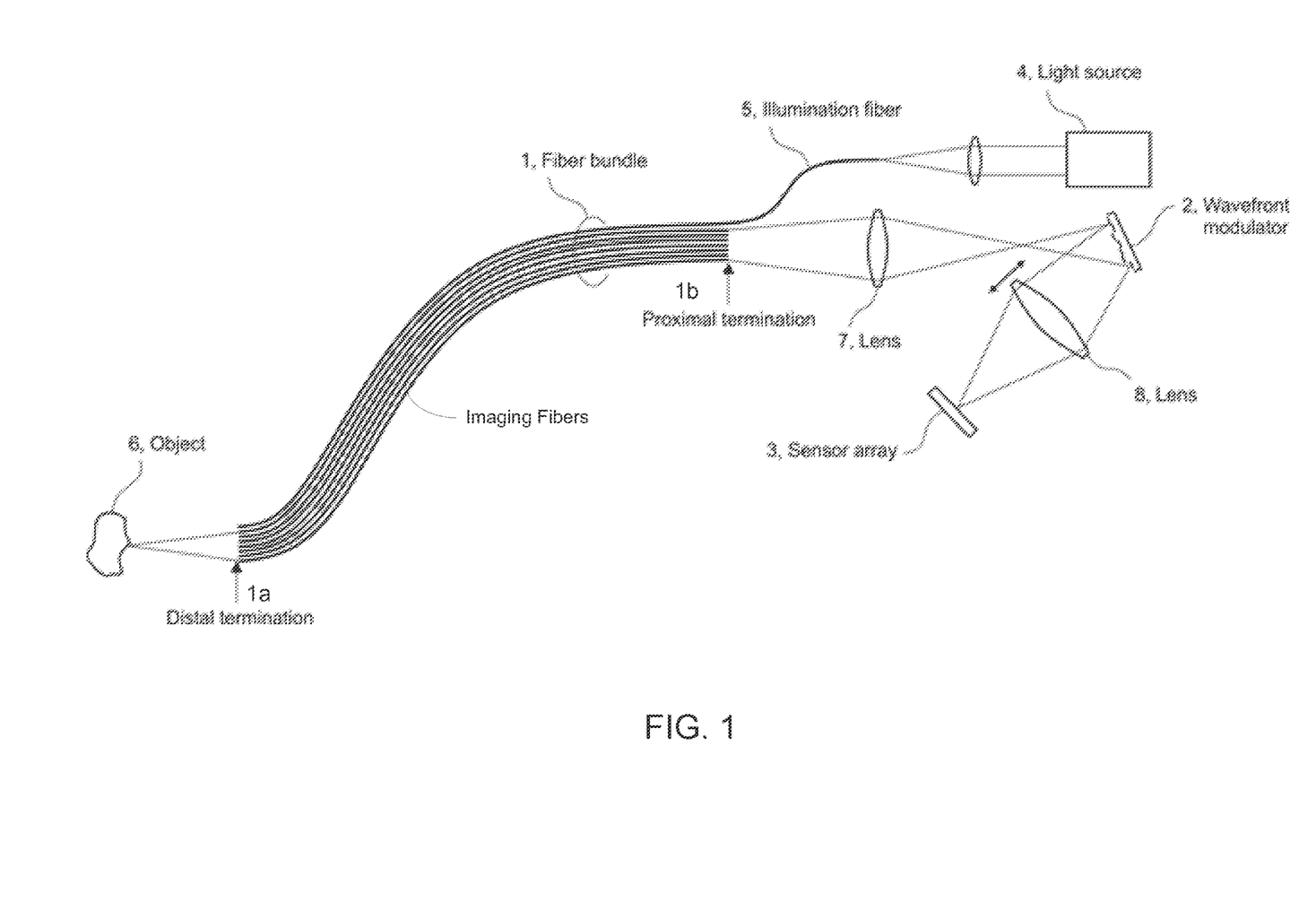
FIG. 1 shows an exemplary optical endoscope based on the disclosed technology by using an optical phase modulator with phase modulation pixels in an optical reflection mode.

FIG. 1 shows an example of a lensless optical endoscope having an optical fiber bundle 1 that includes multiple imaging fibers (e.g., single-mode fibers) and a distal termination 1a for interfacing with a target or object 6 to be imaged and a proximal termination 1b for interfacing with an optical imaging and detection module. Illumination of the scene can be accomplished by including one or more illumination fibers 5, which can be either multi-mode or single-mode, as part of the fiber bundle 1. One or more light sources 4 are provided to generate the illumination light which is guided by the one or more illumination fibers 5 to the distal termination 1a to shine onto an object 6 to be imaged. A coherent light source such as a laser (e.g., a diode laser) can be used as a light source 4. In addition, a light source with low optical coherence, such as certain light-emitting diodes (LEDs) may also be used as the light source 4. The disclosed technology herein uses a phase modulation to reduce the randomness of the optical phases of different optical beams in the imaging fibers in the fiber bundle 1 in the detection module to reconstruct an optical image of the object 6 so that a light source with partial coherence can be used as long the phase modulation is sufficient to remove the randomness of the different beams collected by the imaging fibers. The optical fiber bundle 1 is utilized to collect light directly from an object 6 without using an objective lens. The wavefront of the light from the object 6 is collected in segments by the imaging fibers in the fiber bundle 1 such as single-mode optical fibers which transport the collected wavefront segments to the proximal termination 1b of the fiber bundle 1. Notably, there is not an objective lens at the distal termination 1a for collecting light from the object 6. Each of the wavefront segments exits from the proximal termination 1b with an unknown optical phase relative to other segments transported by the other fibers of the fiber bundle 1. As a consequence, the overall wavefront of the light at the proximal termination 1b is usually aberrated (sometimes highly aberrated), or randomized. Before an image of the scene can be formed, the overall wavefront should regain its coherence: the random optical phases of the wavefront segments are to be eliminated or suppressed below a tolerance level. To accomplish this, a lens, 7, is employed to project the wavefront segments from the proximal termination 1b onto the wavefront modulator, 2, in such way that each wavefront segment (exiting each optical fiber) is projected onto a different pixel of a wavefront modulator 2.

The wavefront modulator 2 is a device that include or possesses a number of segments, or pixels, each of which can be independently adjusted to add or subtract an optical phase for the optical wave that either transmits or reflects from it. In implementations, the wavefront modulator 2 can be an array of phase modulation pixels that either reflect or transmit light where each phase modulation pixel can be individually controlled to produce a desired phase change in the optical beam or wavefront segment that is reflected or transmitted by that phase modulation pixel. In implementations, the pixels of such a wavefront modulator 2 can be controlled through various mechanisms, such as a piezoelectric force, an electrostatic force, or an electromagnetic force; the active component of a pixel can also be a liquid crystal device that changes a phase of light that transmits through the liquid crystal material. Therefore, the phase modulation pixels of the wavefront modulator 2 receive and operate on different wavefront segments of the returned light from the object 6 via different imaging fibers in the fiber bundle 1 to produce modified wavefront segments, respectively. The modified wavefront segments that are produced by the phase modulation pixels of the wavefront modulator 2 are then directed into an optical sensor array 3 of optical sensor pixels for imaging reconstruction.

Figure 2:
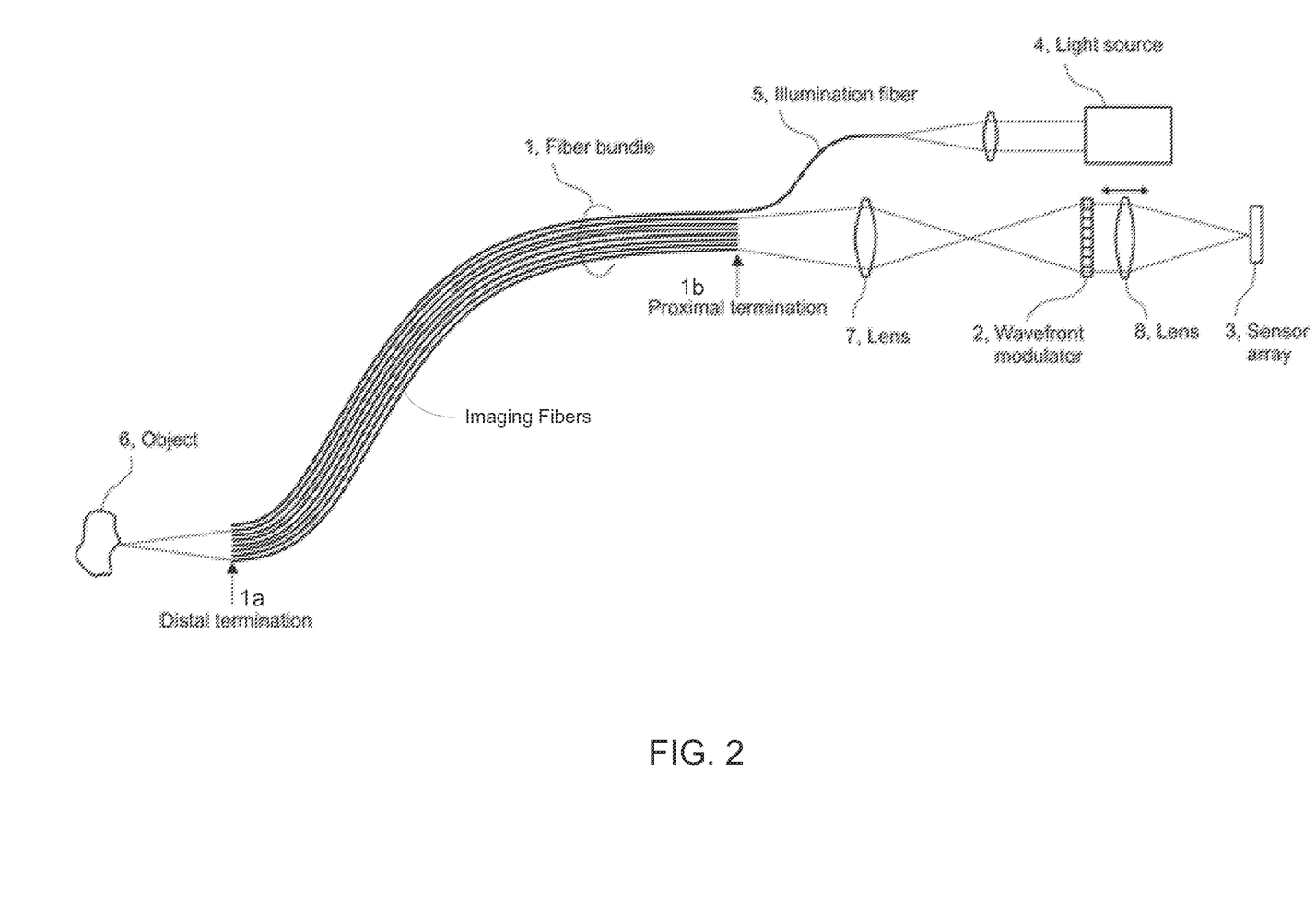
FIG. 2 shows an exemplary optical endoscope based on the disclosed technology by using an optical phase modulator with phase modulation pixels in an optical transmission mode.
Figure 3A:
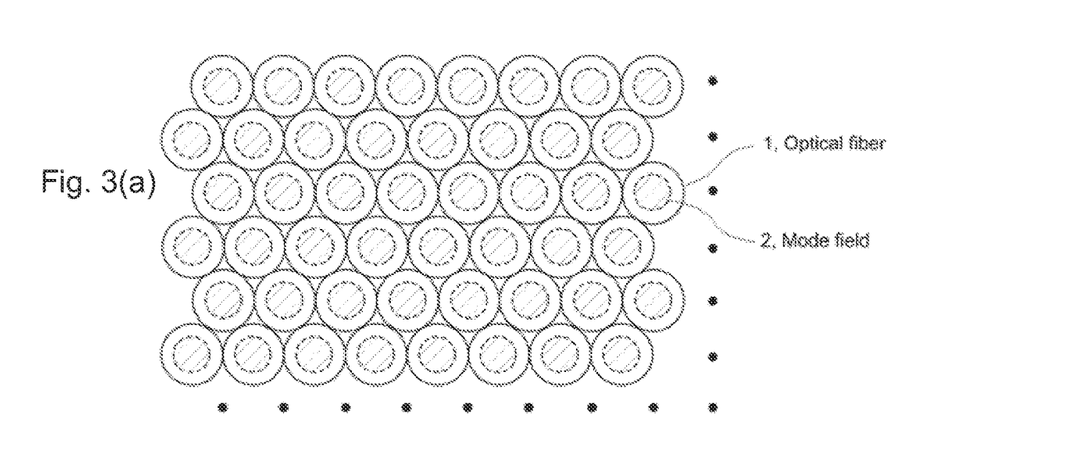
FIGS. 3(a) and 3(b) show two examples of fiber bundle arrangement geometries for the imaging fibers in FIG. 1 or 2.
Figure 3B:
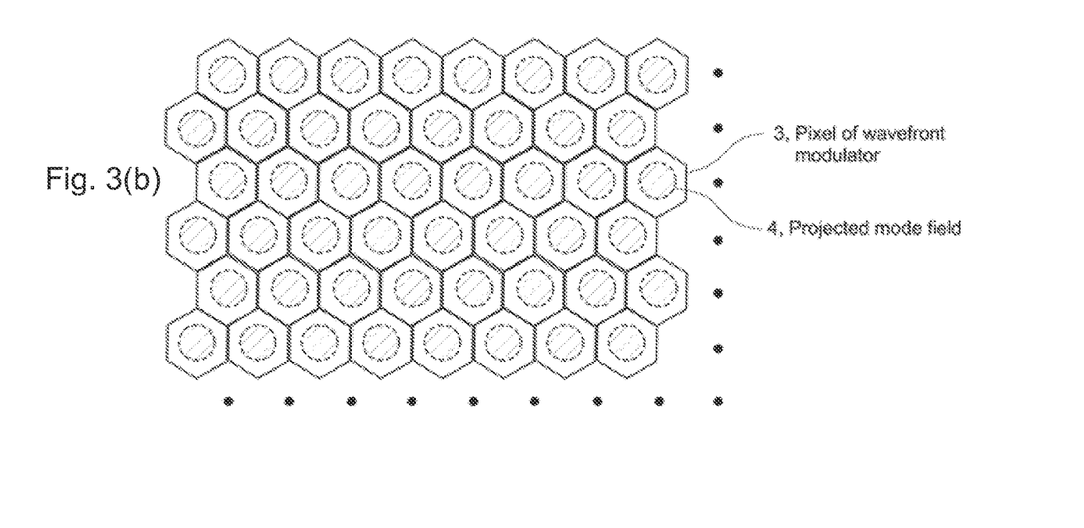

The lensless endoscope in FIG. 1 implements a wavefront modulator 2 in an optical reflection mode and the lensless endoscope in FIG. 2 implements a wavefront modulator 2 in an optical transmission mode. FIG. 3 shows examples of the output wavefront segments at the proximate termination 1b of the fiber bundle 1 in FIG. 1 or 2 where FIG. 3(a) shows one exemplary arrangement of the imaging fibers in the fiber bundle 1 and FIG. 3(b) shows another exemplary arrangement of optical fibers in a hexagonal array in forming a bundle it is convenient to couple such a fiber bundle with a wavefront modulator that possesses hexagonal pixels. Referring to implementations in FIGS. 1 and 2, all the wavefront segments exiting the fiber bundle 1 can be imaged onto their matching pixels in the wavefront modulator 2 with a lens 7.

Figure 4A:
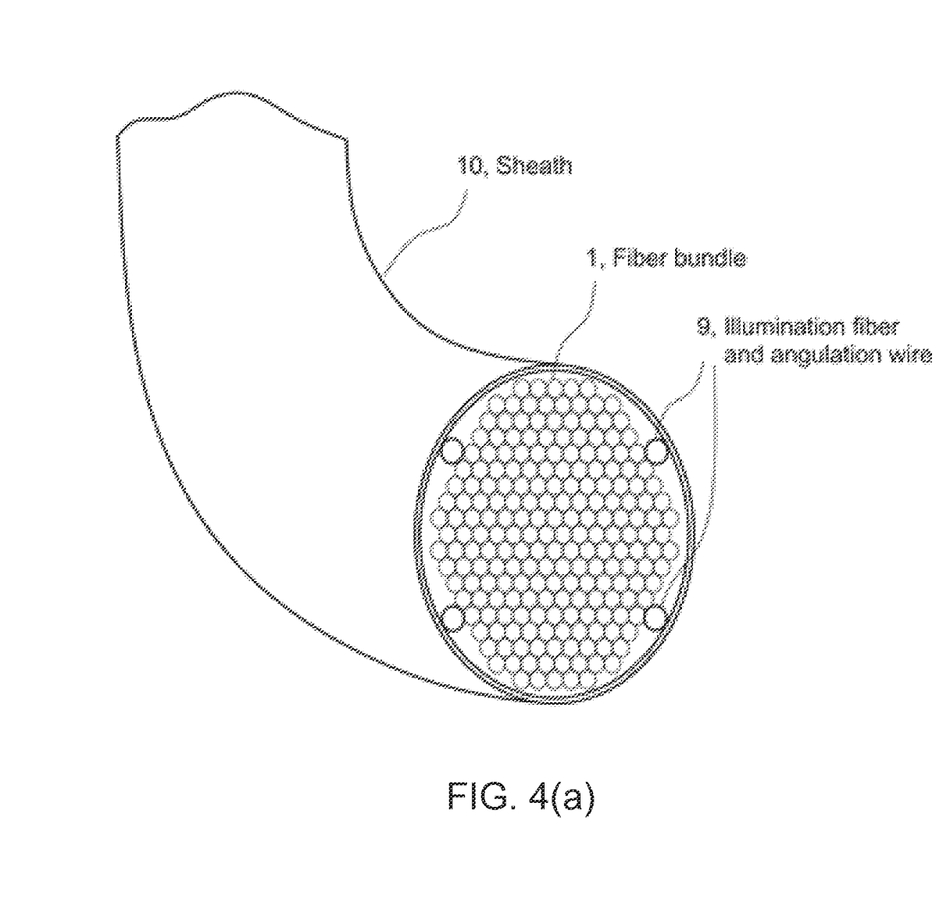
FIGS. 4(a) and 4(b) show two examples of fiber bundle constructions for FIG. 1 or 2.
Figure 4B:
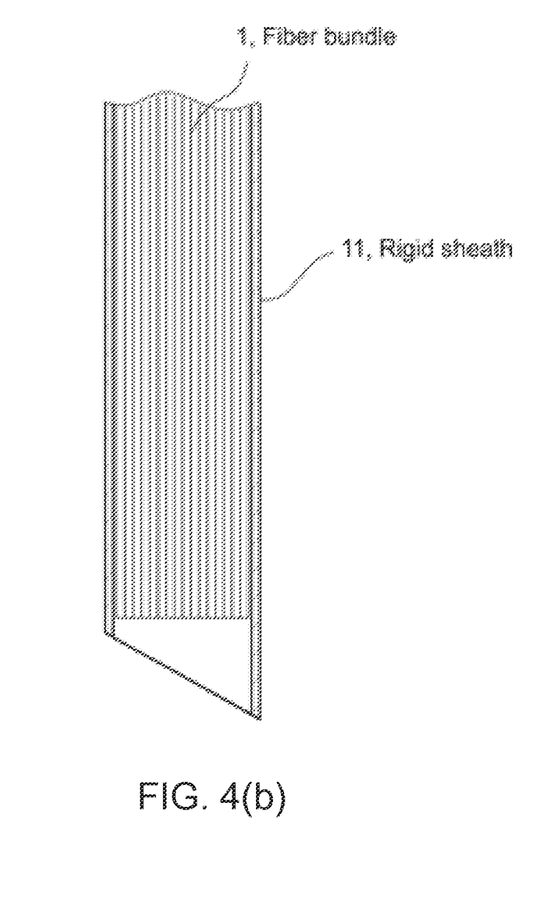

In FIGS. 1 and 2, the fiber bundle 1 includes a sheath to contain the imaging fibers and illumination fibers a bundle. FIG. 4(a) shows a sheath 10 to form a bendable fiber bundle suitable for various imaging applications. FIG. 4(b) shows a rigid sheath 11 to form a rigid fiber bundle 1 suitable for various applications.

In both implementations in FIGS. 1 and 2, to allow images to form properly after the phase modulator 2, the task of the phase modulator 2 is to make all the wavefront segments from the object 6 coherent by adding or subtracting an optical phase to each of the wavefront segments through the action of the individual phase modulation pixels of the wavefront modulator 2. In implementations, a control algorithm can be used to control the pixel phase values produced by the individual phase modulation pixels of the wavefront modulator 2. For example, one of the effective control algorithms for this purpose can be based on the principle of optimizing a metric that is derived from the light-intensity distribution on the sensor array 3. The overall algorithm involves adjusting all the pixels of the wavefront modulator 2 in a coordinated fashion to maximize or minimize the metric. One way of constructing such a metric is through the following formula:

$$\text{Metric} = \sum_{m,n \in area} Mask_{m,n} I_{m,n}, \quad (1)$$

where $I_{m,n}$ is the light intensity of a phase modulation pixel labeled (m, n); and $Mask_{m,n}$ represents a modification in the light intensity or rescales the light intensity of each pixel by a number (e.g., attenuating the light intensity at the pixel). The value assignment of $Mask_{m,n}$ is dependent on the light intensity distribution 4, in the metric area. In one example, the values of $Mask_{m,n}$ are determined in a binary pattern: for those pixels whose light intensities are greater than the average intensity, such a pixel is set to have $Mask_{m,n}=+1$; for all others $Mask_{m,n}=-1$.

One example for setting or controlling the wavefront modulator 2 is a routine that adjusts the pixels of the wavefront modulator 2 in Walsh-function patterns to maximize the above-mentioned metric. Walsh functions are bi-valued functions and can be considered specific assignation of signs (plus and minus) to arrays of discrete numbers, positions, or surface segments.

Figure 5:
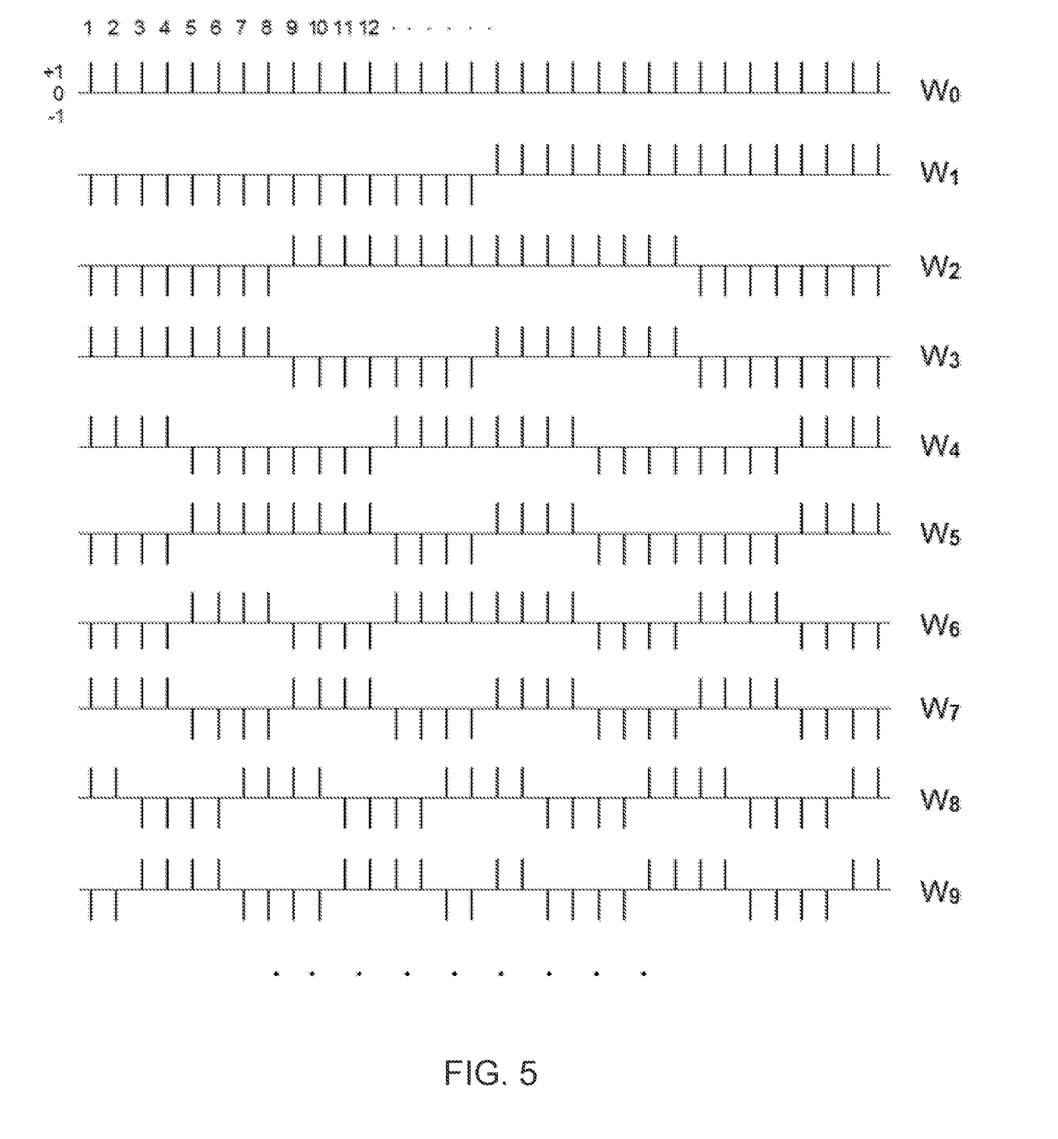
FIG. 5 shows an example of Wash codes for controlling optical phases of different wavefront segments in operating the device in FIG. 1 or 2.

The example shown in FIG. 5 uses Walsh functions for a collection of 32 discrete variables for 32 imaging fibers within the fiber bundle 1 in FIG. 1 or 2.

For a given number of independent control valuables, or degrees of freedom, of a physical system there is always a group of Walsh functions, the total number of which is equal to or greater than the degrees of freedom, that can be used to completely describe the state of the system in the sense that any possible and arbitrary state of the system can be expressed by a superposition of the Walsh functions. For example, an imaging device is equipped with a deformable mirror (a kind of wavefront modulator) that possesses 1000 actuators. Any value assignments for the 1000 control signals can be expressed by a superposition of a group of 1024 Walsh functions as they form a mathematically complete and orthogonal basis set for 1024 numbers, a subset of which (1000 numbers) can be associated the real control signals while the remaining numbers are inconsequential.

In operation, a wavefront modulator exerts a phase modification to an optical wavefront in such a way that a portion of the wavefront, which can include several disconnected parts, experiences a uniform phase change, $\xi$, relative to the remaining portion the light intensity at any position of the imaging array varies in a sinusoidal relationship with $\xi$:

$$I = B_0 + B_1 \cos(\xi + \chi), \quad (2)$$

where $B_0$, $B_1$ and $\chi$ are constants whose values are dependent on the position on the imaging array. It is now easy to see that if $Mask_{m,n}$ in Eq. (1) is kept unchanged while varying $\xi$ the metric of Eq. (1) also varies in a sinusoidal relationship with $\xi$:

$$\text{Metric} = C_0 + C_1 \cos(\xi + \theta) \quad (3)$$

where $C_0$, $C_1$ and $\theta$ are constants so long as the metric boundary and $Mask_{m,n}$ are kept unchanged. Clearly, if a wavefront modulator perturbs a wavefront in a Walsh function form the dependence of the metric on the Walsh-function amplitude $\phi$ is governed by the same relationship as Eq. (3) by replacing $\xi$ with $2\phi$.

Therefore, when the pixels of the wavefront modulator in FIG. 1 is adjusted according to Walsh-function patterns, the relationship between the metric and the Walsh-function amplitude is governed by Eq. (3).

The above relationship between a Walsh-function perturbation to the wavefront and the metric allows for a simple and reliable algorithm that brings optical phases associated with the difference wavefront segments to uniformity, and images of the scene emerge as a result.

Figure 6:
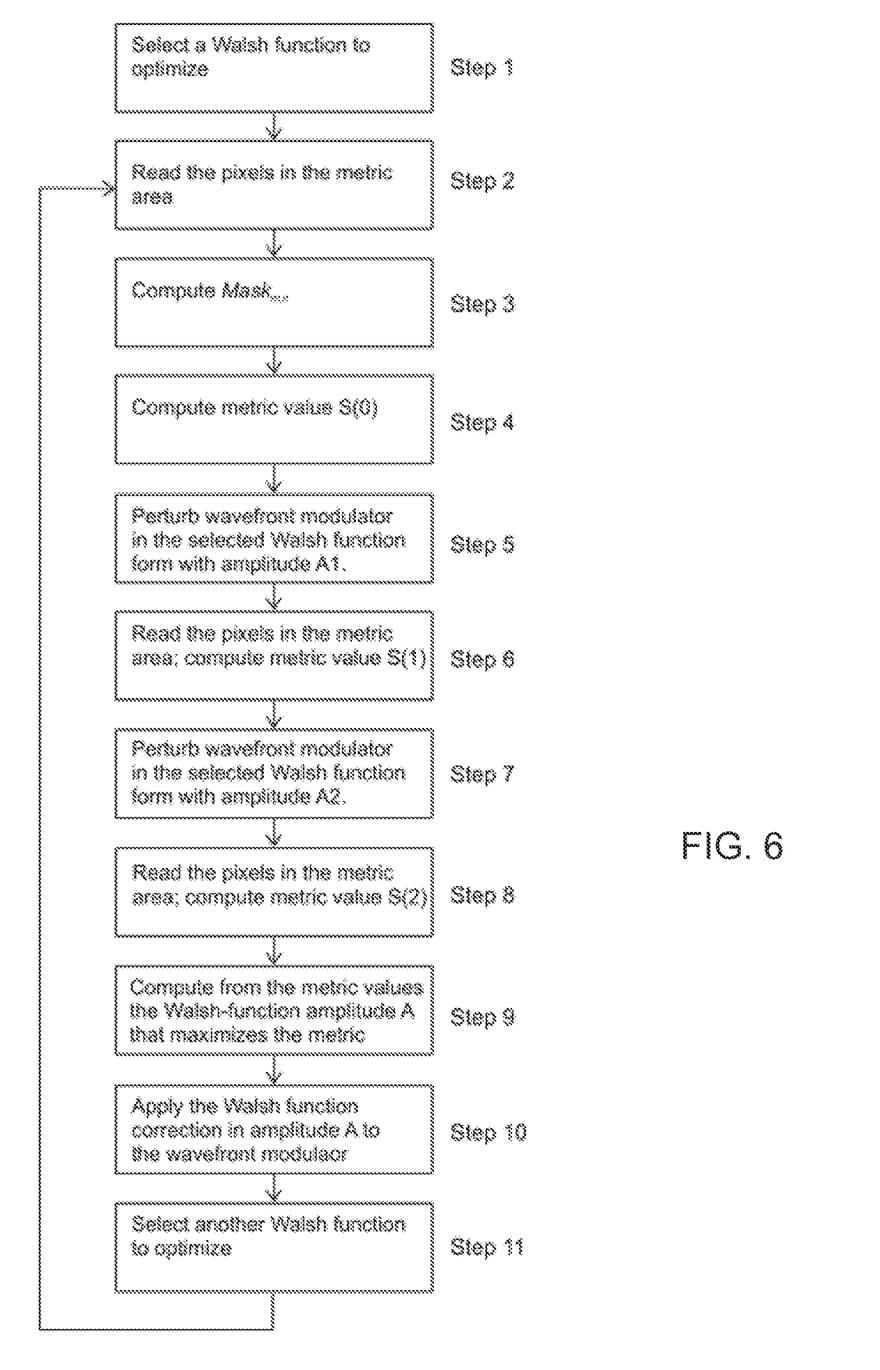
FIG. 6 shows an example of a control operation sequence in operating the device in FIG. 1 or 2.

FIG. 6 shows an example of an operation sequence of the basic steps in a control subroutine for constructing such an algorithm. Notably, $Mask_{m,n}$ computed in Step 3 is used through Step 8 ($Mask_{m,n}$ changes when next Walsh function is selected); this ensures that the relationship between the Walsh-function-perturbation amplitudes and the metric values is governed by Eq. (3) which, in turn, allows the determination of the Walsh-function amplitude that maximizes the metric.

To unify the phases of all the wavefront segments (carried over by the optical fibers) the task is to apply this subroutine to all the Walsh functions associated with the wavefront modulator. When the metric is maximized under all the Walsh functions the phases of all the wavefront segments are unified, thus, a sharply focused image of the scene emerges.

Referring to FIGS. 1 and 2, a lens 8 is provided in the optical path between the phase modulator 2 and the sensor array 3 and can be adjusted. Once the proximal-end wavefront is made coherent (the phases of the segments are made uniform) by the phase modulator 2, the focal distance of the instrument can be varied by moving the lens 8 before the sensor array 3. With this focal adjustment, scenes at various distances from the distal termination 1a of the fiber bundle 1 in FIGS. 1 and 2 can be brought into sharp focus at the sensor array 3.

Wavefront modulators of either reflective or transmissive type can be used as the phase modulator 2. FIG. 2 shows an optical layout for a lensless endoscope with a transmissive wavefront modulator. Illumination of the scene can be accomplished by including one or more illumination fibers, which can be either multi-mode or single-mode, in the fiber bundle as shown in FIGS. 1 and 2. To bend the distal tip of the endoscope one may attach angulation wires to the fiber bundle as shown in FIG. 4(a).

The disclosed lensless endoscope imaging system can also be fashioned into a needle-shaped endoscope with a rigid tip. In some implementations, a large number of imaging fibers can be bundled to provide a large number of imaging pixels for obtaining detailed or high resolution images from a targeted object such as a tissue or an area of an organ inside a person. For example, the disclosed technology can be implemented to allow several thousands of optical fibers to form a bundle in a diameter less than 0.5 mm. In various designs; it is feasible to manufacture needle endoscopes, schematically shown in FIG. 4(b), for transdermal applications.

In some applications, the optical fibers can be arranged into a hexagonal array in forming a bundle as shown in FIG. 3(b). It is convenient to couple such a fiber bundle with a wavefront modulator that possesses hexagonal pixels so that all the wavefront segments exiting the fiber bundle can be imaged onto their matching pixels in the wavefront modulator with a simple lens.

Figure 7:
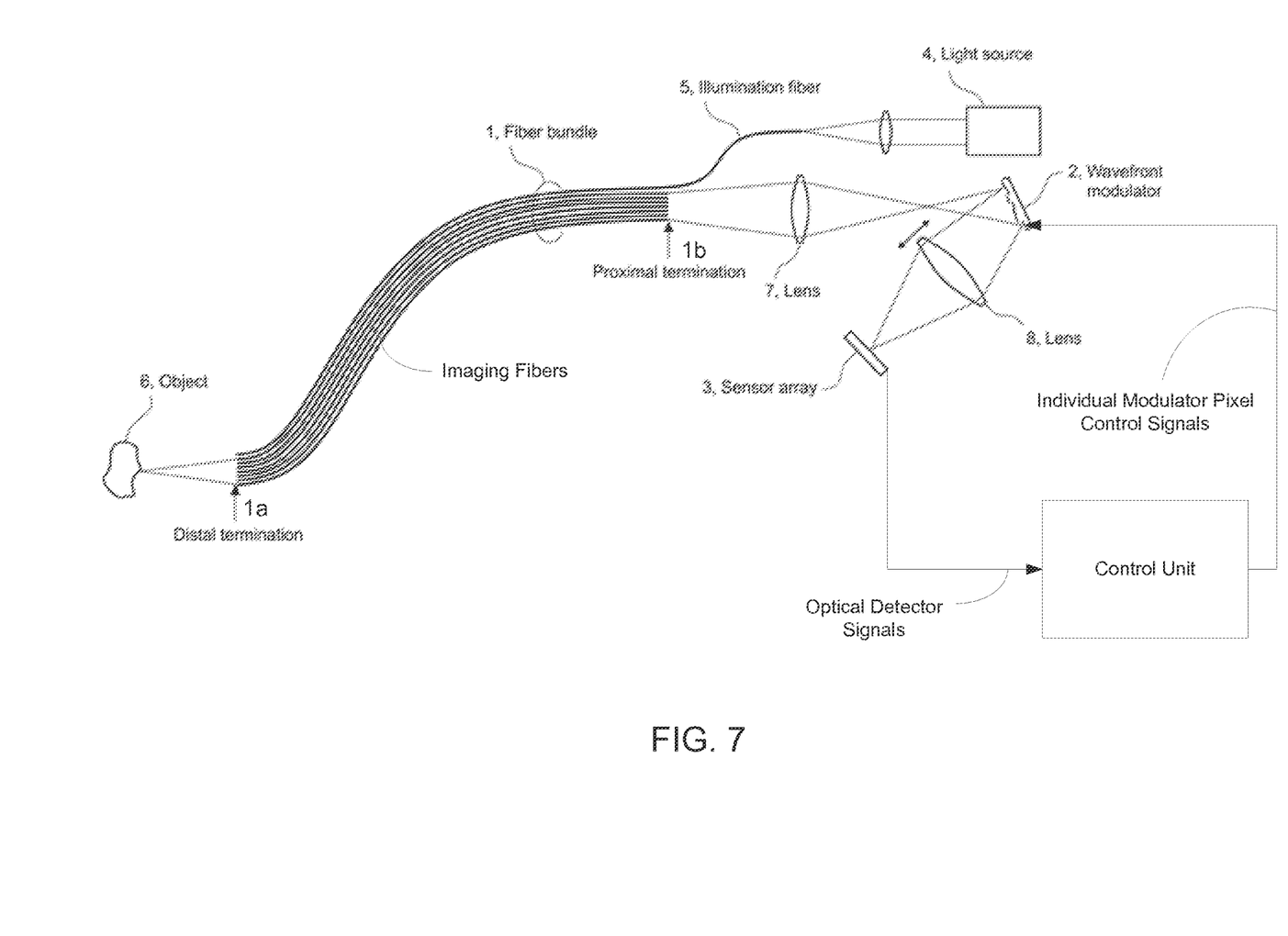
FIG. 7 shows an example of a block diagram of the control circuit for implementing the device in FIG. 1 or 2.

FIG. 7 shows a control unit that is coupled to the optical sensor 3 and the wavefront modulator 2 in the implementation in FIG. 1 or 2 to perform the control operations disclosed in this document, such as the control flow in FIG. 6. The control unit is coupled to the optical sensor 3 to receive the optical detector signals from different pixels in the optical sensor 3. The control unit can include a digital processor such as a microprocessor to use optical detector signals from different pixels in the optical sensor 3 to generate values for $Mask_{m,n}$ for the metric in Steps 3 and 4. The control unit also implements a feedback control as shown by Steps 5 through 8.

The disclosed technology and disclosed embodiments can be used to provide various implementations. For example, an imaging device can include a plurality of optical fibers to directly collect the light emanated by a scene and a wavefront modulator, where the optical fibers subsequently transport the light in segments to a place where said light segments are incident on the wavefront modulator that adds or subtracts an optical phase to each individual segment. The wavefront segments modulated by the wavefront modulator are subsequently focused onto an imaging array. In implementations, the wavefront modulator can be a deformable mirror or a spatial light modulator having a plurality of independently controllable pixels that respond to the commands of a control unit for adding or subtracting spatially variable amount of optical phase to light waves transmitted through or reflected from it.

For another example, an endoscope can be constructed to include a flexible optical fiber bundle whose first termination collects light emanated by a scene without mediation of any lensing element and whose second termination is optically connected to a wavefront modulator in such a way that the light exiting each individual fiber is impinged upon a different pixel of said wavefront modulator that is followed by a focusing element and a sensor array.

For another example, an imaging system can be constructed to include a plurality of waveguides that collect light from a scene with their first terminations and transport the collected light to their second terminations, an array of phase modulation elements each of which receives light from one of said second terminations of the waveguides, a focusing assembly positioned to receive light from the phase modulation elements, a light sensor array positioned in a focal plane of the focusing assembly, and a control unit that is electrically connected to the sensor array to acquire data and is electrically connected to the phase modulation elements to supply control commands.

For another example, a flexible endoscope can be constructed to include an optical fiber bundle having a distal termination for collecting light from a scene to be imaged and a proximal termination for the collected light to exit, a deformable mirror or a spatial light modulator having an array of phase modulation pixels that are optically connected with said proximal termination of said fiber bundle, a focusing assembly positioned to receive light from said deformable mirror or spatial light modulator, a light sensor array positioned in a focal plane of said focusing assembly, and a control unit that is electrically connected to said light sensor array to acquire signals and is electrically connected to said deformable mirror or spatial light modulator to supply control signals. In implementing this flexible endoscope, the control unit can be used to send commands to the deformable mirror or spatial light modulator in such a way that the phases associated with the modulation pixels are varied in Walsh function patterns to maximize or minimize a metric derived from the signals acquired from the sensor array.

For yet another example, a rigid endoscope can be constructed to include a rigid or semi-rigid tubing, an optical fiber bundle having a distal termination inside said tubing for collecting light from a scene to be imaged and a proximal termination for the collected light to exit, a deformable mirror or a spatial light modulator having an array of phase modulation pixels that are optically connected with the proximal termination of the fiber bundle, a focusing assembly positioned to receive light from the deformable mirror or spatial light modulator, a light sensor array positioned in a focal plane of the focusing assembly, and a control unit that is electrically connected to the light sensor array to acquire signals and is electrically connected to the deformable mirror or spatial light modulator to supply control signals.

The disclosed technology can be used to construct imaging devices or systems to examine endoscopically human or animal organs in many branches of medicine including cardiology, pulmonology, gastroenterology, urology, endocrinology, ophthalmology and orthopedics etc. For example, the flexible device can be inserted into a blood vessel for cardiovascular imaging and intervention throughout the body. As a further example, the above-mentioned needle endoscope can be inserted percutaneously to reach interiors of organs such as a peripheral volume of a lung or a kidney.

In implementing the disclosed technology in this patent document, certain features in a PCT publication No. WO 2014/031797 published on Feb. 27, 2014 for "CORRECTING UNDESIRED DISTORTIONS OR ABERRATIONS AND GENERATING DESIRED WAVEFRONTS IN OPTICAL IMAGING, SENSING, SIGNALING AND OTHER APPLICATIONS BASED ON BI-VALUED WALSH FUNCTIONS" based an PCT application No. PCT/US2013056067 filed on Aug. 21, 2013, the entire disclosure of which is incorporated by reference as part of the specification of this patent document.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An endoscope that uses light to image a scene or an object, comprising:
   one or more light sources to produce illumination light;
   a fiber bundle that includes a distal termination end and a proximal termination end, one or more illumination optical fibers that receive the illumination light from the one or more light sources at the proximal termination end to guide the illumination light to the distal termination end to illuminate a scene or object to be imaged, and a plurality of imaging optical fibers that directly collect light from the scene or object at the distal termination end without using a lensing element to collect light from the scene or the object into the distal termination end and guide the collected light to the proximal termination end;
   a wavefront modulator including a plurality of independently controllable phase modulation pixels to produce independently controllable phases, respectively, the wavefront modulator positioned relative to the proximal termination end of the fiber bundle to receive the collected light from the imaging optical fibers in such a way that the collected light exiting different imaging optical fibers is impinged upon different phase modulation pixels of the wavefront modulator, respectively, to produce phase-modulated light segments corresponding to the imaging optical fibers, respectively;
   an optical sensor array of optical detectors located to receive the phase-modulated light segments from the wavefront modulator and to produce detector outputs carrying image information of the scene or object; and
   a control unit coupled to the wavefront modulator to control the wavefront modulator, wherein the independently controllable pixels of the wavefront modulator respond to control commands of the control unit to add or subtract a spatially variable amount of an optical phase to a phase-modulated light segment, wherein the control unit operates to use a metric based on the detector outputs of the optical detectors of the optical sensor array to generate the feedback control to each of the independently controllable pixels of the wavefront modulator, and the control unit operates to generate feedback control signals for the independently controllable pixels of the wavefront modulator, respectively, based on a set of Walsh functions that respectively correspond to the plurality imaging optical fibers, one Walsh function per imaging optical fiber.

2. The endoscope of claim 1, wherein:
   the wavefront modulator includes a deformable mirror having a plurality of independently controllable reflector pixels that produce the phase-modulated light segments by optical reflection.

3. The endoscope of claim 1, wherein:
   the wavefront modulator includes a spatial light modulator in which independently controllable pixels transmit light to produce the phase-modulated light segments.

4. The endoscope of claim 1, comprising:
   a control unit coupled to the wavefront modulator to control the wavefront modulator, and
   wherein the independently controllable pixels of the wavefront modulator respond to control commands of the control unit to add or subtract a spatially variable amount of an optical phase to a phase-modulated light segment.

5. The endoscope of claim 4, wherein:
   the control unit operates to use a metric based on outputs of the optical detectors of the optical sensor array to generate the feedback control to each of the independently controllable pixels of the wavefront modulator.

6. The endoscope of claim 5, wherein:
   the control unit operates to generate feedback control signals for the independently controllable pixels of the wavefront modulator, respectively, based on Walsh codes.

7. The endoscope of claim 1, wherein:
   each light source produces coherent light or partially coherent light for illuminating the scene or object to be imaged.

8. The endoscope of claim 1, wherein:
   the fiber bundle includes a rigid sheath that encloses the one or more illumination optical fibers and the plurality of imaging optical fibers at the distal termination end.

9. The endoscope of claim 1, wherein:
   the fiber bundle includes a flexible sheath that encloses the one or more illumination optical fibers and the plurality of imaging optical fibers at the distal termination end.

10. The endoscope of claim 1, wherein the endoscope is configured for cardiology imaging to use the distal termination end to image an area of a person's heart.

11. The endoscope of claim 1, wherein the endoscope is configured for pulmonology imaging to use the distal termination end to image an area of a person's lung.

12. The endoscope of claim 1, wherein the endoscope is configured for gastroenterology imaging to use the distal termination end to image an area of a person's gastrointestinal tract.

13. The endoscope of claim 1, wherein the endoscope is configured for urology imaging to use the distal termination end to image an area of a person's urinary tract.

14. The endoscope of claim 1, wherein the endoscope is configured for endocrinology imaging to use the distal termination end to image an area of a person's endocrine gland.

15. The endoscope of claim 1, wherein the endoscope is configured for ophthalmology imaging to use the distal termination end to image an area of a person's eye.

16. The endoscope of claim 1, further comprising:
   a lens located between the wavefront modulator and the optical sensor array to project the phase-modulated light segments onto the optical sensor array.

17. The endoscope of claim 1, wherein the one or more illumination optical fibers extend beyond the proximal termination end of the plurality of imaging optical fibers.

18. The endoscope of claim 1, wherein the one or more illumination optical fibers and the plurality of imaging optical fibers are contained in a sheath such that the one or more illumination optical fibers are disposed externally to the plurality of imaging optical fibers.

19. An endoscope that uses light to image a scene or an object, comprising:
one or more light sources to produce illumination light;
a fiber bundle that includes a distal termination end and a proximal termination end, one or more illumination optical fibers that receive the illumination light from the one or more light sources at the proximal termination end to guide the illumination light to the distal termination end to illuminate a scene or an object to be imaged, and a plurality of imaging optical fibers that directly collect light from the scene or object at the distal termination end without using a lensing element to collect light from the scene or object into the distal termination end and guide the collected light to the proximal termination end;
a wavefront modulator including a plurality of independently controllable phase modulation pixels to produce independently controllable phases, respectively, the wavefront modulator positioned relative to the proximal termination end of the fiber bundle to receive the collected light from the imaging optical fibers in such a way that the collected light exiting different imaging optical fibers is impinged upon different phase modulation pixels of the wavefront modulator, respectively, to produce phase-modulated light segments corresponding to the imaging optical fibers, respectively; and
an optical sensor array of optical detectors located to receive the phase-modulated light segments from the wavefront modulator and to produce detector outputs carrying image information of the scene or object,
wherein the imaging optical fibers are different in structure from the one or more illumination fibers and are not coupled to receive the illumination light from the one or more light sources.

20. The endoscope of claim 19, wherein the wavefront modulator includes a deformable mirror having a plurality of independently controllable reflector pixels that produce the phase-modulated light segments by optical reflection.

21. The endoscope of claim 19, wherein:
the fiber bundle includes a sheath that encloses the one or more illumination optical fibers and the plurality of imaging optical fibers at the distal termination end.

22. The endoscope of claim 19, wherein the endoscope is configured for cardiology imaging to use the distal termination end to image an area of a person's heart.

23. The endoscope of claim 19, wherein the endoscope is configured for pulmonology imaging to use the distal termination end to image an area of a person's lung.

24. The endoscope of claim 19, wherein the endoscope is configured for gastroenterology imaging to use the distal termination end to image an area of a person's gastrointestinal tract.

25. The endoscope of claim 19, wherein the endoscope is configured for urology imaging to use the distal termination end to image an area of a person's urinary tract.

26. The endoscope of claim 19, wherein the endoscope is configured for endocrinology imaging to use the distal termination end to image an area of a person's endocrine gland.

27. The endoscope of claim 19, wherein the endoscope is configured for ophthalmology imaging to use the distal termination end to image an area of a person's eye.

28. An endoscope that uses light to image a scene or an object, comprising:
one or more light sources to produce illumination light;
a fiber bundle that includes a distal termination end and a proximal termination end, one or more illumination optical fibers that receive the illumination light from the one or more light sources at the proximal termination end to guide the illumination light to the distal termination end to illuminate a scene or an object to be imaged, and a plurality of imaging optical fibers that directly collect light from the scene or object at the distal termination end without using a lensing element to collect light from the scene or object into the distal termination end and guide the collected light to the proximal termination end;
a wavefront modulator including a plurality of independently controllable phase modulation pixels to produce independently controllable phases, respectively, the wavefront modulator positioned relative to the proximal termination end of the fiber bundle to receive the collected light from the imaging optical fibers in such a way that the collected light exiting different imaging optical fibers is impinged upon different phase modulation pixels of the wavefront modulator, respectively, to produce phase-modulated light segments corresponding to the imaging optical fibers, respectively; and
an optical sensor array of optical detectors located to receive the phase-modulated light segments from the wavefront modulator and to produce detector outputs carrying image information of the scene or object,
wherein the wavefront modulator is positioned relative to the proximal termination end of the fiber bundle to receive the collected light from the imaging optical fibers without receiving or interacting with the illumination light from the one or more illumination fibers so that the illumination light is guided and directed by the one or more illumination optical fibers in the fiber bundle from the one or more light sources to the scene or object to be imaged without being modulated by the wavefront modulator.

29. The endoscope of claim 28, wherein the wavefront modulator includes a deformable mirror having a plurality of independently controllable reflector pixels that produce the phase-modulated light segments by optical reflection.

30. The endoscope of claim 28, wherein:
the fiber bundle includes a sheath that encloses the one or more illumination optical fibers and the plurality of imaging optical fibers at the distal termination end.

31. The endoscope of claim 28, wherein the endoscope is configured for cardiology imaging to use the distal termination end to image an area of a person's heart.

32. The endoscope of claim 28, wherein the endoscope is configured for pulmonology imaging to use the distal termination end to image an area of a person's lung.

33. The endoscope of claim 28, wherein the endoscope is configured for gastroenterology imaging to use the distal termination end to image an area of a person's gastrointestinal tract.

34. The endoscope of claim 28, wherein the endoscope is configured for urology imaging to use the distal termination end to image an area of a person's urinary tract.

35. The endoscope of claim 28, wherein the endoscope is configured for endocrinology imaging to use the distal termination end to image an area of a person's endocrine gland.

36. The endoscope of claim 28, wherein the endoscope is configured for ophthalmology imaging to use the distal termination end to image an area of a person's eye.

37. An endoscope that uses light to image a scene or object, comprising:
one or more light sources to produce illumination light;
a fiber bundle that includes a distal termination end and a proximal termination end, one or more illumination optical fibers that receive the illumination light from the one or more light sources at the proximal termination end to guide the illumination light to the distal termination end to illuminate a scene or object to be imaged, and a plurality of imaging optical fibers that directly collect light from the scene at the distal termination end without using a lensing element to collect light from the scene or object into the distal termination end and guide the collected light to the proximal termination end;
a wavefront modulator including a plurality of independently controllable phase modulation pixels to produce independently controllable phases, respectively, the wavefront modulator positioned relative to the proximal termination end of the fiber bundle to receive the collected light from the imaging optical fibers in such a way that the collected light exiting different imaging optical fibers is impinged upon different phase modulation pixels of the wavefront modulator, respectively, to produce phase-modulated light segments corresponding to the imaging optical fibers, respectively; and
an optical sensor array of optical detectors located to receive the phase-modulated light segments from the wavefront modulator and to produce detector outputs carrying image information of the scene or object;
the imaging optical fibers are coupled to collect light from the scene or object to be imaged and are not coupled to receive the illumination light from the one or more light sources; and
the wavefront modulator is not coupled to intercept or interact with the illumination light carried by the one or more illumination optical fibers in the fiber bundle so that the illumination light is guided and directed by the one or more illumination optical fibers in the fiber bundle from the one or more light sources to the scene or object to be imaged without being modulated by the wavefront modulator.

38. The endoscope of claim 37, wherein the wavefront modulator includes a deformable mirror having a plurality of independently controllable reflector pixels that produce the phase-modulated light segments by optical reflection.

39. The endoscope of claim 37, wherein:
the wavefront modulator includes a spatial light modulator in which independently controllable pixels transmit light to produce the phase-modulated light segments.

40. The endoscope of claim 37, wherein:
each light source produces coherent light or partially coherent light for illuminating the scene or object to be imaged.

41. The endoscope of claim 37, wherein:
the fiber bundle includes a rigid sheath that encloses the one or more illumination optical fibers and the plurality of imaging optical fibers at the distal termination end.

42. The endoscope of claim 37, wherein:
the fiber bundle includes a flexible sheath that encloses the one or more illumination optical fibers and the plurality of imaging optical fibers at the distal termination end.

43. The endoscope of claim 37, wherein the endoscope is configured for cardiology imaging to use the distal termination end to image an area of a person's heart.

44. The endoscope of claim 37, wherein the endoscope is configured for pulmonology imaging to use the distal termination end to image an area of a person's lung.

45. The endoscope of claim 37, wherein the endoscope is configured for gastroenterology imaging to use the distal termination end to image an area of a person's gastrointestinal tract.

46. The endoscope of claim 37, wherein the endoscope is configured for urology imaging to use the distal termination end to image an area of a person's urinary tract.

47. The endoscope of claim 37, wherein the endoscope is configured for endocrinology imaging to use the distal termination end to image an area of a person's endocrine gland.

48. The endoscope of claim 37, wherein the endoscope is configured for ophthalmology imaging to use the distal termination end to image an area of a person's eye.

49. The endoscope of claim 37, further comprising:
a lens located between the wavefront modulator and the optical sensor array to project the phase-modulated light segments onto the optical sensor array.

* * * * *